United States Patent [19]

Kirk et al.

[11] Patent Number: 5,200,328

[45] Date of Patent: * Apr. 6, 1993

[54] PROCESS FOR PRODUCING METHYL GLYCOSIDE ESTERS

[75] Inventors: Ole Kirk, Copenhagen; Sven Erik Godtfredsen, Vaerlose, both of Denmark; Fredrik Björkling, Helsingborg, Sweden

[73] Assignee: Novo Nordisk A/S, Bagsvaerd, Denmark

[*] Notice: The portion of the term of this patent subsequent to Mar. 2, 2010 has been disclaimed.

[21] Appl. No.: 494,702

[22] Filed: Mar. 16, 1990

[30] Foreign Application Priority Data

Feb. 17, 1989 [DK] Denmark .............................. 0768/89

[51] Int. Cl.$^5$ ............................................. C12P 19/04
[52] U.S. Cl. ..................................... 435/101; 435/198; 435/219; 435/252.1; 435/252.3; 435/931; 435/874; 536/115; 536/119
[58] Field of Search ............ 435/101, 198, 219, 252.1, 435/253.3, 931, 874; 536/115, 119

[56] References Cited

U.S. PATENT DOCUMENTS

| | | | |
|---|---|---|---|
| 3,597,417 | 8/1971 | Myhre | 260/234 |
| 4,614,718 | 9/1986 | Seino et al. | 435/72 |
| 4,687,843 | 8/1987 | Smolin et al. | 536/18.3 |
| 4,719,178 | 1/1988 | Macrae et al. | 435/135 |

FOREIGN PATENT DOCUMENTS

| | | |
|---|---|---|
| 62-195292 | 8/1987 | Japan . |
| 195292 | 8/1987 | Japan .................... 435/101 |
| 62-289190 | 12/1987 | Japan . |
| 63-112993 | 5/1988 | Japan . |

OTHER PUBLICATIONS

Sweers et al. *J. Am. Chem. Soc.*, vol. 108 (1986), pp. 6421–6422.

Lazar et al., *Proceedings American Oil Chemists' Society*, "World Conference on Emerging Technologies in the Fats and Oils Industry," Ed. Baldwin, pp. 346–354, 1986.

Hansen et al., *Proceedings Am. Oil Chem. Soc.*, "World Conf. on Emerging Technologies in the Fats and Oils Ind.," Ed. Baldwin, pp. 365–370, 1986.

*Primary Examiner*—Johnnie R. Brown
*Assistant Examiner*—Pamela S. Webber
*Attorney, Agent, or Firm*—Steve T. Zelson; Elias J. Lambiris

[57] ABSTRACT

Fatty acid esters of methyl glycosides are prepared by reacting a fatty acid or ester with a methyl glycoside in the presence of an enzyme catalyst, in particular a lipase. The resulting fatty acid esters are preferably monoesters.

The methyl glycoside fatty acid esters may be used as surface-active agents in cleaning compositions or personal care products.

11 Claims, No Drawings

PROCESS FOR PRODUCING METHYL GLYCOSIDE ESTERS

FIELD OF INVENTION

The present invention relates to an enzyme-catalyzed process for preparing methyl glycoside esters, and cleaning compositions and personal care compositions comprising such esters.

BACKGROUND OF THE INVENTION

Surface-active agents constitute an extremely important class of industrial chemicals which have a wide variety of uses, for instance as detergents for washing purposes, as emulsifiers in food products and as active ingredients in various personal care products such as shampoos, soaps or creams.

At the molecular level, surface-active agents are substances which are characterized by the presence of hydrophobic and hydrophilic regions within each individual surfactant molecule and which owe their ability to reduce surface tension to this particular structure. The combination of hydrophobic and hydrophilic regions within the same molecule may be obtained in many different ways, for instance by combining a sulphonic acid residue, a quaternized ammonium moiety or a glycerol moiety with an alkyl chain as is the case with the linear alkyl surfactants, the quaternized alkyl amines or the monoglycerides, respectively. When designing a surfactant molecule, the detailed molecular architecture of the compounds is a major concern, care being taken to achieve a precise balance between the hydrophobic and hydrophilic regions of the surfactant molecules as well as to achieve a favorable spatial arrangement of these individual regions of the molecules. Apart from this, the possibility of producing surface-active agents by high-yielding processes and on the basis of inexpensive and readily available raw materials is always carefully considered The environmental issues related to the eventual loading of the surfactant into the environment are finally a matter of major concern.

As a result of these considerations, many researchers have shown considerable interest in the production of surface-active agents based on sugars and fatty acids, e.g. sugar esters. Such substances were expected to exhibit surface-active properties due to the hydrophilic properties of the sugar moieties and the hydrophobic properties of the fatty acid residues The balance between hydrophobic and hydrophilic properties might be varied by modifying the sugar and/or the fatty acid by adding a number of substituents. Such surface-active agents could be produced from very inexpensive starting materials and, being prepared from and degradable into naturally occurring components, they would not constitute an environmental hazard.

One traditional method of preparing sugar esters, including glycoside esters, has been by transesterification. Thus, U.S. Pat. No. 3,597,417 discloses the preparation of alkyl monoglycoside esters by transesterification in a two-step process by reacting a glycoside with a short-chain ester and subsequently with a fatty acid ester. Another method is disclosed in U.S. Pat. No. 2,759,922 in which a process for producing esterified glycosides, e.g. methyl glycoside, by reacting the glycoside with a fatty acid at a temperature of 160°–300° C.

In spite of the intensive interest in producing sugar esters of fatty acids, it has been found rather difficult to produce surface-active sugar esters by conventional synthesis procedures Among other things, this is due to the presence of several chemically similar groups in the sugar molecules which may therefore be esterified at many different positions and to varying degrees when exposed to esterification reagents. Sugar esters prepared by traditional chemical synthesis are therefore inhomogeneous in that they are composed of mixtures of compounds different in the degree of esterification and in the position of the acyl groups on the sugar moiety. This may cause differences in the surface-active properties of the compounds. As, additionally, the preparation of sugar esters by conventional chemical synthesis has been found to be rather cost-intensive, the currently available sugar esters prepared by these methods have found limited application only.

In view of the difficulties encountered in the production of sugar esters by chemical synthesis and in view of the attractiveness of these compounds as surface-active agents, alternative methods have been suggested for the production of esterified sugars, one interesting method involving the use of enzymes which are known to be highly regioselective and enantioselective so that they may be employed for the selective esterification of one or more hydroxy groups on the sugar molecules. Such enzymatic processes may exploit cheap starting materials which means that the resulting sugar esters are inexpensive even though they are of a high quality.

The attempts to develop efficient enzymatic syntheses of sugar esters have so far not been particularly successful. Thus, Sweers and Wong (J. Amer. Chem. Soc. 108, 1986, pp. 6421–6422) briefly discuss the regioselective esterification of sugars, e.g. methyl glycoside, with pentanoic acid in the presence of a Candida cylindracea lipase and report that the yield of this process was very low (2–3%). Similarly, U.S. Pat. No. 4,614,718 discloses the preparation of sugar or sugar alcohol esters by reacting the sugar or sugar alcohol with a higher fatty acid in finely divided or emulsified form in the presence of lipase until an equilibrium is obtained. A large amount of water is used as solvent and as a result of this, the equilibrium of the reaction cannot be shifted which means that the yield cannot be optimized Furthermore, the reaction proceeds for a considerable length of time even though large amounts of the enzyme are employed.

One reason why poor yields are obtained and/or long reaction times are required in the known enzymatic processes is the considerable difference in polarity between the sugar component and the fatty acid component which makes it difficult to find a solvent in which both are soluble. When using water as a solvent as taught in U.S. Pat. No. 4,614,718, the fatty acid is not dissolved resulting in an inefficient reaction and a low utilization of the fatty acid reagent. Few solvents for both sugars and fatty acids are available (e.g. dimethylformamide) and such solvents will generally inactivate the enzyme and are in most cases toxic, constituting an environmental hazard.

JP 62-195 292 discloses a method of preparing sugar or sugar alcohol esters by reacting a sugar or sugar alcohol with a fatty acid in an aqueous medium in the presence of a lipase after which the water is gradually removed and incubation is continued. JP 62-289 190 discloses a method of preparing sugar or sugar alcohol esters by mixing sugar or sugar alcohol, fatty acid and lipase and adding only a minor amount of water to the reaction mixture JP 63-112 993 discloses a method of preparing sugar or sugar alcohol esters by reacting an acetylated sugar or sugar alcohol with a fatty acid in an organic solvent in the presence of a lipase.

An object of the present invention is to provide a process for the production of methyl glycoside esters in high yields from inexpensive materials by enzymatic catalysis without the use of toxic solvents.

Another object of the invention is to provide methyl glycoside esters which are particularly useful as surface-active agents in cleaning compositions and personal care products.

SUMMARY OF THE INVENTION

Accordingly, the present invention relates to a process for preparing a compound of the general formula I $$(R-COO)_n-X-OCH_3$$

wherein R is alkyl with 4-24 carbon atoms optionally substituted by hydroxy or halogen, X is a carbohydrate comprising 1-3 monosaccharide units, and n is 1, 2 or 3, the process comprising reacting an acid or ester of the general formula II $$R-COOR^1$$

wherein R is as defined above and $R^1$ is H or lower alkyl, with a glycoside of the general formula III $$X-OCH_3$$

as defined above, in the presence of an enzyme catalyst.

In another aspect, the invention relates to a personal care composition which comprises a compound of the general formula I as defined above.

In a further aspect, the present invention relates to a cleaning composition comprising a non-ionic surfactant including a compound of the general formula I as defined above.

DETAILED DESCRIPTION OF THE INVENTION

In the general formula I, a preferred meaning of n is 1, corresponding to monoesters of the formula I'

$$R-COO-X-OCH_3 \qquad (I')$$

wherein R and X are as defined above The process of the invention is believed to be the only process by which it is possible to prepare methyl glycoside monoesters of formula I'in an acceptable purity.

Compared to the processes disclosed in JP 62-195 292 and JP 62-289 190 for enzymatically preparing sugar or sugar alcohol esters, the reaction times required to prepare methyl glucoside esters of formula I by the present process are significantly lower. The present process therefore represents an important economic advantage. Furthermore, it results in a high yield of regiospecifically esterified monoesters of formula I (e.g. 6–0 monoesters of methyl glucoside) due to the use of methyl glycosides as starting reactants rather than free sugars (or sugar alcohols) the use of which may lead to the formation of a mixture of mono-, di-, tri-, etc. esters. The production of monoesters of formula I in a high yield is desirable as these compounds have been found to be particularly useful for detergent purposes, as demonstrated below (Example 8).

Each monosaccharide unit in the carbohydrate X is preferably in pentose or hexose form, in particular in cyclic (furanose or pyranose) form. The carbohydrate X in the glycoside moiety X—OCH$_3$ is preferably a monosaccharide Examples of suitable monosaccharides are glucose, fructose, ribose, galactose, mannose, arabinose or xylose.

When a disaccharide is employed as the carbohydrate X, it may be selected from the group consisting of sucrose, lactose, maltose, isomaltose and cellobiose.

In a preferred embodiment of the process of the invention, the reaction of the fatty acid II with the glycoside III proceeds in a substantially non-aqueous medium. Thus, the reaction may proceed in a suitable organic solvent (such as hexane or acetonitrile) or, in a particularly preferred embodiment, substantially in the absence of a solvent which is to say that the fatty acid or ester II acts as a solvent for the glycoside III (it should be noted that a minor amount of water may be present bound to the enzyme to ensure a satisfactory reactivity of the enzyme). By proceeding in a substantially non-aqueous medium such as in the absence of a solvent, it is possible to shift the equilibrium in the reaction of the fatty acid II with the glycoside III towards formation of the end product, thus improving the yield of the compound (I).

Although the pure α-anomer may be employed in the process of the invention, it has been found advantageous that at least a certain proportion of the glycoside moiety X—OCH$_3$ is in β-anomeric form as this anomer has surprisingly been found to be more reactive than the α-anomer in the present process. The greater reactivity of the β-anomer is believed to be ascribable to its considerably greater solubility in organic solvents, in case the fatty acid II, resulting in a more rapid and complete reaction and hence a higher yield of the methyl glycoside ester. In order to obtain the advantageous effect of including the β-anomer, the anomer should therefore be included in a mixture of the α- and β-anomeric forms of the glycoside III in an amount of at least 10% and preferably at least 20%, such as between 20 and 99%, by weight of the mixture. The pure β-anomer may also be employed with highly satisfactory results (a yield of the methyl glycoside ester of about 95% vide example 1).

R is preferably alkyl with 6-22 carbon atoms. Thus, R—COO—may suitably be selected from the group consisting of hexanoyl, heptanoyl, octanoyl, nonanoyl, decanoyl, dodecanoyl, tetradecanoyl, hexadecanoyl, octadecanoyl, eicosanoyl, docosanoyl, cis-9-octadecenoyl, cis,cis-9,12-octadecadienoyl or cis,cis,cis-9,12,15-octadecatrienoyl R—COO—may further be selected from the group consisting of arachinoyl, arachidonoyl and behenoyl.

Accordingly, preferred compounds (I) prepared by the process of the invention may be selected from the group consisting of methyl 6-O-hexanoylglucoside, methyl 6-O-heptanoylglucoside, methyl 6-O-octanoylglucoside, methyl 6-O-nonanoylglucoside, methyl 6-O-decanolyglucoside, methyl 6-O-dodecanoylglucoside, methyl 6-O-tetradecanoylglucoside, methyl 6-O-hexadecanoylglucoside, methyl 6-O-octadecanoylglucoside, methyl 6-O-eicosanoylglucoside, methyl 6-O-docosanoylglucoside, methyl 6-O-cis-9-octadecenoylglucoside, methyl 6-O-cis,cis-9,12-octadecadienoylglucoside and methyl 6-O-cis,cis,cis-9,12,15-octadecatrienoylglucoside.

Enzymes which may be useful as catalysts in the process of the invention are those which catalyze hydrolysis of ester bonds, i.e. hydrolases. Such enzymes may be lipases, esterases or proteases, in particular lipases which may be defined as enzymes catalyzing reactions involving ester bonds, e.g. hydrolysis, synthesis and/or exchange of ester bonds. Lipases which may be employed in the present process may be porcine pancreatic lipase or microbial lipases produced, for instance, by strains of Asoerqillus, Enterobacterium, Chromobacterium, Geotricium or Penicillium. Preferred lipases for use according to the invention are those produced by species of Mucor (e.g. Lipozyme TM), Humicola, Pseudomonas or Candida.

Particularly preferred lipases are those produced by the following strains of microorganisms, all of which have been deposited in the Deutsche Sammlung von Mikroorganismen in accordance with the provisions of the Budapest Treaty on the International Recognition of the Deposit of Microorganisms for the Purposes of Patent Procedure:

*Candida antarctia,* deposited on Sep. 29, 1986, with the number DSM 3855, and on 8 December 1986, with the numbers DSM 908 and DSM 3909.

*Pseudomonas cephacia,* deposited on Jan. 30, 1987, with the number 3959

*Humicola lanuginosa,* deposited on Aug. 13, 1986 and May 4, with the deposit numbers 3819 and 4109, respectively

*Humicola brevispora,* deposited on May 4, 1987, with the deposit number DSM 4110,

*Humicola brevis var. thermoidea,* deposited on May 4, 1987, with the deposit number DSM 4111, and

*Humicola insolens,* deposited on Oct. 1, 1981, with the deposit number DSM 1800.

Currently preferred lipases are those produced by *Candida antarctica,* DSM 3855, DSM 3908 and DSM 3909. These enzymes may be produced by the process disclosed in WO 88/02775. Briefly, the Candida strains in question are cultivated under aerobic conditions in a nutrient medium containing assimilable carbon and nitrogen sources as well as essential minerals, trace elements etc., the medium being composed according to established practice in the art. After cultivation, liquid enzyme concentrates may be prepared by removing insoluble materials, e.g. by filtration or centrifugation, after which the broth is concentrated by evaporation or reverse osmosis Solid enzyme preparations may be prepared from the concentrate by precipitation with salts or water-miscible solvents, e.g. ethanol, or by drying such as spray-drying in accordance with well-known methods.

Additional lipases may be obtained from the following strains which are publicly available without restriction from the Centraalbureau voor Schimmelculturen (CBS), American Type Culture Collection (ATCC), Agricultural Research Culture Collection (NRRL) and Institute of Fermentation, Osaka (IFO) with the following deposit numbers: Candida antarctica, CBS 5955, ATCC 34888, NRRL Y-8295, CBS 6678, ATCC 28323, CBS 6821 and NRRL Y-7954; *Candida tsukubaensis,* CBS 6389, ATCC 24555 and NRRL Y-7795; *Candida auriculariae,* CBS 6379, ATTC 24121 and IFO 1580; *Candida humicola,* CBS 571, ATCC 14438, IFO 0760, CBS 2041, ATCC 9949, NRRL Y-1266, IFO 0753 and IFO 1527; and *Candida foliorum,* CBS 5234 and ATCC 18820.

It is known to produce lipase by recombinant DNA techniques, cf. for instance EP 238 023 or EP 305 216. Recombinant lipases may also be employed for the present purpose.

When employed in the process of the invention, the enzyme may be in a soluble state. It is, however, preferred to immobilize the enzyme in order to facilitate the recovery of the methyl glycoside esters (I) produced by the present process and in order to obtain a better enzyme utilization as the immobilized enzyme may be recycled. Immobilization procedures are well known (cf. for instance K. Mosbach, ed., "Immobilized Enzymes", *Methods in Enzymology* 44, Academic Press, NY, 1976) and include cross-linking of cell homogenates, covalent coupling to insoluble organic or inorganic supports, entrapment in gels and adsorption to ion exchange resins or other adsorbent materials. Coating on a particulate support may also be employed (cf. for instance A.R. Macrae and R.C. Hammond, *Biotechnology and Genetic Engineering Reviews* 3, 1985, p. 193). Suitable support materials for the immobilized enzyme are, for instance, plastics (e.g. polystyrene, polyvinylchloride, polyurethane, latex, nylon, teflon, dacron, polyvinylacetate, polyvinylalcohol or any suitable copolymer thereof), polysaccharides (e.g. agarose or dextran), ion exchange resins (both cation and anion exchange resins), silicon polymers (e.g. siloxane) or silicates (e.g. glass).

It is preferred to immobilize the enzyme on an ion exchange resin by adsorbing the enzyme to the resin or by cross-linking it to the resin by means of glutaraldehyde or another cross-linking agent in a manner known per se. A particularly preferred resin is a weakly basic anion exchange resin which may be a polystyrene-, polyacrylic- or phenol-formaldehydetype resin. Examples of commercially available polyacrylictype resins are Lewatit$^{(R)}$ E 1999/85 (produced by Bayer, Federal Republic of Germany) and Duolite$^{(R)}$ ES-568 (produced by Rohm & Haas, Federal Republic of Germany) Immobilization of enzymes to this type of resin may be carried out according to EP 140 542. Immobilization to phenyl-formaldehyde-type resins may be done according to DK 85/878.

Another convenient material for immobilizing enzymes is an inorganic support, such as a silicate. The enzyme may be attached to the support by adsorption or by covalent coupling, eg. as described in K. Mosbach, ed., op.cit.

The process of the invention may advantageously proceed at a low pressure such as a pressure below about 0.05 bar, in particular below about 0.01 bar. The reaction temperature is conveniently in the range of about 20°–100° C., preferably about 30°–80° C.

When the reaction is complete, the compound (I) may be recovered by filtering off the (immobilized) enzyme, and excess fatty acid II may be removed by, for instance, short path distillation in a manner known per se.

It has surprisingly been found that when included in personal care compositions according to the invention, the surface-active compounds (I) exhibit advantageous properties, in particular with respect to imparting desirable foaming characteristics to such compositions. In particular, it has been found that when R in formula I is alkyl with 7–10 carbon atoms, and in particular when R—COO is octanoyl, and/or when the carbohydrate X in formula I is a monosaccharide, in particular glucose, a favorable foaming of the personal care composition is produced when in use. Thus, a preferred example of a compound (I) for inclusion in the composition of the invention is methyl 6-O-octanoylglucoside. The compound (I) may be one prepared by the process described above, and may be present in a mixture of α- and β-anomers as described above.

Examples of personal care compositions of the invention are shampoos, toothpastes, shaving creams or liquid soaps, constituting a class of products where foaming is considered to be important, cf. for instance *Journal of the Society of Cosmetic Chemists* 10, 1960, pp. 390–414.

A shampoo composition of the invention (e.g. a hair or body shampoo) may contain the methyl glucoside ester (I) as the principal or sole surfactant, in which case it is usually present in an amount of 1–25% by weight of the composition. However, the composition may further comprise an anionic surfactant in an amount of 5–35%, in particular 10–25%, by weight of the composition.

Examples of suitable anionic surfactants for inclusion in shampoos are alkyl ether sulphonates, alkyl sulphates (e.g with 10–22 carbon atoms in the alkyl chain), alkyl polyethoxy sulphonates (e.g. with 10–18 carbon atoms in the alkyl chain), α-olefin sulphonates (e.g. with 10–24 carbon atoms), α-sulphocarboxylates (e.g. with 6–20 carbon atoms) and esters thereof (prepared with, e.g., $C_1$–$C_{14}$ alcohols), alkyl glyceryl ether sulphonates (e.g. with 10–18 carbon atoms in the alkyl chain), fatty acid monoglyceride sulphates and sulphonates, alkyl phenol polyethoxy ether sulphates (e.g. with 8–12 carbon atoms in the alkyl chain), 2-acyloxy-1-sulphonates (e.g. with 2–9 carbon atoms in the acyl group and 9–22 carbon atoms in the alkane moiety) and β-alkyloxy alkane sulphonates (e.g. with 1–3 carbon atoms in the alkyl group and 8–20 carbon atoms in the alkane moiety).

If an anionic surfactant is included in the composition of the invention, the compound (I) is suitable present in an amount of 1–20% by weight of the composition.

The shampoo composition of the invention may additionally comprise a foam booster, for instance a fatty acid dialkanoyl amide, an N-acyl amino acid or a betain derivative in an amount of 0.1–20% by weight of the composition.

If a higher viscosity of the shampoo composition is desired, it is possible to include a suitable thickener such as, for instance, carboxy methyl cellulose or, if the anionic surfactant is an alkyl ether sulphonate, the viscosity may be regulated by means of a salt, e.g. NaCl.

In accordance with the invention, a typical shampoo composition may be formulated as follows

| | |
|---|---|
| Methyl glycoside ester | 1–20% |
| Anionic surfactant | 10–20% |
| Foam booster | 0.1–10% |
| Salt | 0–5% |
| Thickener | 0–5% |
| Acid, to adjust to | pH 4–7 |
| Perfume | q.s. |
| Preservative | q.s. |
| Water | balance |

When the composition of the invention is a toothpaste composition, it may contain the compound (I) in an amount of 1–20% by weight, in addition to conventional ingredients such as gelling agents, thickeners, abrasives, bulk agents and the like.

When the composition of the invention is a liquid soap composition, it may contain the surface-active compound (I) in an amount of 1–20%, in addition to conventional ingredients such as anionic surfactants, foam boosters and the like.

Similarly, a shaving cream composition of the invention may contain 1–20% by weight of the methyl glycoside ester (I) in addition to conventional ingredients.

Apart from this, it has been found that compounds of the general formula I exhibit good cleaning properties In particular, it has surprisingly been found that monoesters of fatty acids with methyl glycoside are highly efficient as surface-active agents in cleaning compositions, especially for removing fatty soils. Accordingly, the present invention further relates to a cleaning composition comprising an effective amount of a non-ionic surfactant comprising a compound of the general formula I'

$$R\text{—}COO\text{—}X\text{—}OCH_3 \qquad (I')$$

wherein R and X are as defined above Preferred compounds (I') are those wherein X is a monosaccharide.

The monosaccharide in the glycoside moiety may be a pentose or hexose, but is preferably a monohexose. Out of economical considerations, the monohexose is preferably glucose, galactose or fructose, i.e. the glycoside is preferably a glucoside, a galactoside or a fructoside. The monosaccharide X may be in the furanose or pyranose form as indicated above. Due to the ease of preparation, the most accessible of the isomers is preferred, e.g. a glucopyranoside, a galactopyranoside or a fructofuranoside.

When the monosaccharide $X^1$ is a monohexose, the ester bond linking the group R—COO—to the monohexose is preferably attached in the 6-position of the monohexose The cleaning composition of the invention may be formulated in any convenient form, for instance as a powder, a liquid etc. Typical examples of cleaning compositions according to the invention are laundry detergents, dishwash detergents and hard-surface cleaners. More specific examples are liquid heavy duty detergents (with or without phosphate builders) and powder heavy-duty detergents (with or without phosphate builders).

The surfactant in the cleaning composition of the invention may be mainly of the non-ionic type (e.g at least 80% by weight of non-ionic surfactant), or may be a combination of a non-ionic (e.g 20–80% by weight) and another type of surfactant (e.g. 20–80% by weight of, e.g., an anionic, cationic and/or zwitterionic surfactant). Examples of anionic surfactants are linear alkyl benzene sulfonates (LAS), fatty alcohol sulfates, fatty alcohol ether sulfates (AES), alphaolefin sulfonates (AOS) and soaps.

The non-ionic surfactant in the cleaning composition of the invention may be composed mainly of (e.g. at least 80% by weight) a methyl glycoside monoester (I') as described above, or it may be a combination of the methyl glycoside monoester (I') (e.g. 20–80% by weight) and one or more other nonionic surfactants. Examples of such other non-ionic surfactants are alkyl polyethyleneglycol ethers or nonylphenol polyethyleneglycol ethers.

Liquid and powder detergents according to the invention (suitable for the prevalent washing conditions in Western Europe, Japan and USA, respectively) may be formulated substantially as described in "Frame formulations for liquid/powder heavy-duty detergents" (J.Falbe Surfactants in Consumer Products Theory, Technology and Application, Springer-Verlag 1987) by replacing all or part (e.g. 50%) of the non-ionic surfactant with one or more alkyl glycoside mono-esters (I) as described above.

Thus, as described by J. Falbe, supra, a liquid heavy-duty detergent according to the invention may comprise anionic surfactants, non-ionic surfactants, suds controlling agents, foam boosters, enzymes, builders, formulation aids, optical brighteners, stabilizers, fabric softeners, fragrances, dyestuffs and water. Similarly, a powder heavy-duty detergent according to the invention may comprise anionic surfactants, nonionic surfactants, suds controlling agents, foam boosters, chelating agents, ion exchangers, alkalis, cobuilders, bleaching agents, bleach activators, bleach stabilizers, fabric softeners, antiredeposition agents, enzymes, optical brighteners, anticorrosion agents, fragrances, dyestuffs and blueing agents, formulation aids, fillers and water.

The present invention is further illustrated in the following examples which are not in any way intended to be limiting to the scope of the invention for which protection is sought.

EXAMPLES

General procedures

Satisfactory $^1$H and $^{13}$C NMR-spectra were obtained for all compounds. The spectra were recorded on a Bruker WM 400 spectrometer with TMS as internal reference in organic solvents. In D$_2$O the water signal at delta=4.8 was used as internal standard. HPLC-analysis was performed on a Shimadzu LC-4A instrument (refractive index detector) using a Merck LiChrosorb NH$_2$-column and 96 % ethanol as eluent. Preparative liquid chromatography was performed on SiO$_2$ with a gradient of n-pentane, ethyl acetate and methanol as eluent.

EXAMPLE 1

Preparation of methyl 6-O-dodecanoyl β-D-glucopyranoside.

To a mixture of methyl-β-(D)-glucopyranoside (400 g, 2.06 mol, Sigma Chemicals) and dodecanoic acid (620 g, 3.10 mol) in a stirred batch reactor at 80° C. was added an immobilized lipase derived from *Candida antarctica* (20 g, prepared as described in Examples 1 and 19 in W088/02775). Stirring was continued under reduced pressure (0.01 bar) and the progress of the ester synthesis was monitored by HPLC. After 21 hours the enzyme was removed by filtration (at 80° C.). The synthesis of the title compound is shown schematically in Scheme 1 appended hereto. Excess fatty acid was removed by repeated short path distillation (105° C., 4·10$^{-2}$ mbar) yielding 75 % (580 g) crude product along with 5 % β-(D)-glucopyranoside and 20 % diester (HPLC analysis). The crude product was purified by chromatography and identified by NMR spectroscopy.

EXAMPLE 2

Preparation of methyl 6-O-decanoyl-D-glucopyranoside.

Methyl-D-glucopyranoside (19.8 g, 0.10 mol, a 1:1 mixture of methyl α-(D)-glucopyranoside and methyl β-(D)-glucopyranoside, both Sigma Chemicals) was esterified with dodecanoic acid (31 g, 0.15 mol) by the procedure described in Example 1, using 3 g of an immobilized lipase (derived from *Candida antarctica*). The reaction was complete in 24 hours (HPLC showed >90% conversion) and the enzyme was removed by filtration. Purification by chromatography provided the title compound in a yield of 79% (30 g) as a crystalline powder, m.p. 70°–72° C.

EXAMPLE 3

Preparation of methyl 6-O-decanoyl-D-glucopyranoside.

Methyl-D-glucopyranoside (a 2:3 mixture of the α- and β-anomers) (24 g, 0.12 mol, prepared according to Example 6) was esterified with decanoic acid (43 g, 0.25 mol) by the procedure described in Example 1 using 2.4 g of an immobilized lipase (derived from *Candida antarctica*). After 17 hours the enzyme was removed by filtration (at 80° C.) HPLC analysis of the crude product showed 77% of the title compound, 15% diesters and 8% methyl-D-glucopyranoside. Part of the crude product was purified by chromatography, yielding 39.4 g (59%) of the title compound which was identified by NMR spectroscopy.

EXAMPLE 4

Preparation of methyl 6-O-octanoyl-α-D-glucopyranoside

Methyl α-D-glucopyranoside (20.0 g, 0.10 mol, prepared according to Example 6), was esterified with octanoic acid (29.7 g, 0.21 mol) by the procedure described in Example 1 using 6.0 g of an immobilized lipase (from Candida antarctica) as a catalyst. After 36 hours HPLC analysis showed 77% conversion (65% monoester, 12% diester). The reaction was stopped by filtering off the enzyme. Part of the crude product was purified by chromatography yielding 10.7 g (32.4%) of the title compound which was identified by NMR spectroscopy.

EXAMPLE 5

Preparation of methyl 6-O-dodecanoyl-D-glucopyranoside.

To a mixture of methyl-D-glucopyranoside (a 2:3 mixture of the α and ⊕ anomers)(150 g, 0.77 mol, prepared according to example 6) and dodecanoic acid (209 g, 1.05 mol) in a stirred batch reactor at 80° C. was added immobilized lipase (10 g, derived from *Candida antarctica*). Stirring was continued under reduced pressure (0.01 bar) and the progress of the ester synthesis was monitored by HPLC.

After 18 hours methyl-α-D-glucopyranoside (64 g, 0.33 mol, prepared according to example 6), dodecanoic acid (90 g, 0.45 mol) and 6 g lipase were added. After additional 22 hours the enzyme was removed by filtration and the product was worked up by short path distillation according to example 1, yielding a crude product containing 84% 6-O-dodecanoyl-D-glucopyranoside 9% methyl-D-glucoside and 7% diesters Part of the product was purified by chromatography and the identity of the title compound (being a ca 1:1 mixture of the anomers) was confirmed by NMR spectroscopy.

EXAMPLE 6

Preparation of methyl D-glucopyranoside.

α-D-glucose (500 g, 2.78 mol) and a strongly acidic cation exchange resin (100 g Amberlyst 15, BDH Chemicals) was suspended in methanol (1500 ml, 37.1 mol). The mixture was stirred at 65° C. for 68 hours. The progress of the reaction was followed by HPLC. $^1$H NMR analysis of the reaction mixture showed a 1:1 ratio of the α-and β-anomers. The ion exchange resin was removed by filtration and the solution was cooled to 4° C. The crystalline methyl α-D-glucopyranoside was removed by filtration (230 g, 43%) and the mother liquor was evaporated in vacuo to give a crude methyl D-glucopyranoside (304 g, 57%) as a thick syrup ($^1$H NMR showed a ratio between α- and β-anomers of ⅔).

EXAMPLE 7

Foaming

In this example, the methyl-D-glucoside ester was prepared according to Example 4. AES (alkyl ether sulphate) denotes sodium lauryl ether sulphate (Berol 452, Berol Kemi AB, Sweden). CDE indicates coconut acid diethanolamide (Empilan CDE, Albright & Wilson, United Kingdom).

Three commercial Sucrose esters from Mitsubishi Kasei Food Corporation, Japan were used. Their catalogue gives the composition as follows:

| Trade name | Fatty acid | % monoester | % di,tri,polyester |
|---|---|---|---|
| Ryoto L595 | 95% dodecanoic | 30% | 70% |
| — L1570 | 70% — | 70% | 30% |
| — L1695 | 95% — | 80% | 20% |

Determination of foaming

In the following foaming was determined by the method of L. Moldovanyi, W. Hungerbühler, B. Lange: Kosmetika, vol. 5, pp. 37–42 (1977). In this method, air is bubbled through the test solution, and the time to fill a certain volume with foam is noted. Thus, a shorter filling time indicates better foaming.

The detailed conditions were as follows:

| Air flow | 15 liters/min |
|---|---|
| Volume of test solution: | 500 ml |
| Inner diameter of air inlet tube: | 5 mm |
| Volume of foam collected: | 2 liters |
| Inner diameter of foam tube: | 26 mm |

Foaming of single surfactants

Foaming was measured in 2% solutions (as active material). The results are shown below:

| | Surfactant | Filing time |
|---|---|---|
| This invention | Methyl 6-0-octanoyl-D-glucopyranoside | 60 seconds |
| Reference | glucosyl-hexanoate | 900 seconds |
| | Ryoto L595 | *) |
| | Ryoto L1570 | 328 seconds |
| | Ryoto L1695 | 276 — |
| | AES | 175 — |
| | CDE | 180 — |

*) Measurement was not possible, as the surfactant was not sufficiently soluble.

It appears that the compound of the invention shows excellent foaming, even better than AES, the commonly used surfactant in shampoos.

The commercial sucrose esters were chosen to represent the carbohydrate esters of prior-art shampoos that are most closely similar to the esters of the invention, and to represent various ratios of monoester to higher esters. It appears that foaming of sucrose esters used in the prior art is far inferior to that of the methyl glucoside ester of the invention.

EXAMPLE 8

Washing experiments

The glycolipids used in this example were all prepared by a procedure similar to Example 3 and were thus a ca 2:3 mixture of the α- and β-anomer. The coconut fatty acid mixture applied for preparing methyl 6-O-coconut fatty acyl-D-glucoside contained 1% decanoic acid, .51% dodecanoic acid, 24% tetradecanoic acid, 17% octadecanoic add, 5% cis-9-octadecenoic acid and 2% cis,cis,9–12-octadecadienoic acid.

Heavy duty powder detergents with and without phosphate builders were formulated as follows:

Basic phosphate containing detergent (without surfactant): sodium tripolyphosphate 415 g, sodium metasilicate 95 g, carboxy methyl cellulose (CMC) 12 g, EDTA 2.4 g, sodium sulfate 475 g (amounts are indicated as grams per kg of the basic detergent)

Basic non-phosphate containing detergent without surfactant: Zeolit A 265 g, nitrilotriacetic acid 106 g, sodium metasilicate 85 g, CMC 11 g, EDTA 2.1 g, sodium sulfate 425 g.

To the basic detergents was added surfactant (nonionic/LAS in a ratio of 33:67) to a final concentration of 12.5% (w/w) of the phosphate containing detergent and 11.3% of the non-phosphate containing detergent The detergents were applied in concentrations of 4.8 g/1 and 5.3 g/1, respectively.

Washing experiments were performed in a Terg-0-tometer under the following conditions:

| Temperature: | 25° C. |
|---|---|
| Time: | 20 min. |
| Water: | 9° dH (German degrees Hardness) |
| pH: | 9.5 |
| Test swatches: | EMPA 112 (7 × 7 cm)*) |
| Sud ratio: | 7 swatches per 700 ml of washing suds |

*)EMPA 112 swatches (available from EMPA, Switzerland) are soiled with coco, milk fat and sugar.

After washing, residual amounts of fat were determined after Soxhlet extraction and expressed as the percentage of fat by weight of the swatch.

The following results were obtained:

| | Residual fat in % | |
|---|---|---|
| Surfactant (mixed with LAS) | Phosphate | Non-phosphate |
| Berol 160 | 1.96 | 1.97 |
| Hodag CB-6 | 1.97 | 1.95 |
| Methyl-6-0-decanoyl-glucoside | 1.75 | 1.85 |
| Methyl-6,2-O-didecanoyl-glucoside | 2.03 | 2.06 |
| Methyl-6-0-dodecanoyl-glucoside | 1.88 | 1.93 |
| Methyl-6,2-O-didodecanoyl-glucoside | 2.02 | 2.07 |
| Methyl-6-0-tetradecanoyl-glucoside | 1.93 | 1.82 |
| Methyl-6,2-O-ditetradecanoyl-glucoside | 2.02 | 1.98 |
| Methyl-6-0-coconut fatty acyl-glucoside | 1.77 | 1.86 |
| Methyl-6,2-0-di(coconut fatty acyl)-glucoside | 2.02 | 2.00 |

Berol 160 is a commercial alcohol ethoxylate from the Swedish company Berol AB, with a chain length in the fatty alcohol part of $C_{12-14}$ and degree of ethoxylation of 6EO. It is an example of a widely used non-ionic surfactant with a good fat removing effect.

Hodag CB-6 is a methyl glucoside ester mixture based on fatty acids from coconut oil which is a mixture of unspecified mono-, di-, tri-, etc. esters, available from Hodag Corporation, Skokie, IL, USA.

It appears from the table that monoesters of methylglycosides exhibit a superior fat removal effect compared to the corresponding diesters and Hodag CB-6.

We claim:

1. A process for preparing a compound of formula I

R—COO—X—OCH$_3$  (I)

wherein

R is alkyl with 7-24 carbon atoms optionally substituted by hydroxy or halogen; and X is a monosaccharide containing one hexose or pentose unit which carries (a) the —OCH$_3$ group at the anomeric carbon atom and (b) the R—COO— group at a primary hydroxy group; comprising reacting (a) an acid or ester of formula II

R—COOR$^1$  (II)

wherein

R is as defined above; and

R$^1$ is H or lower alkyl; with (b) a glycoside of formula III

X—OCH$_3$  (III)

wherein

X is as defined above; in a substantially non-aqueous medium, in the substantial absence of a solvent other than the acid or ester of formula II acting as a solvent for the glycoside of formula III, and in the presence of an immobilized lipase.

2. A process according to claim 1, wherein X is glucose, fructose, ribose, galactose, arabinose, xylose or mannose.

3. A process according to claim 1, wherein the lipase is produced by a microorganism selected from the group consisting of *Mucor, Humicola, Pseudomonas* or *Candida.*

4. New A process according to claim 3, wherein the lipase is produced by a microorganism selected from the group consisting of *Candida antarctica, Pseudomonas cephalic, Humicola lanuginosa, Humicola brevispora, Humicola brevis var. thermoidea or Humicola insolens.*

5. A process according to claim 4, wherein the lipase is produced by the microorganism *Candida antarctica.*

6. A process according to claim 1, wherein R—COO—is octanoyl, nonanoyl, decanoyl, deodecanoyl, tetradecanoyl, hexadecanoyl, octadecanoyl, eicosanoyl, docosanoyl, cis-9-octadecanoyl, cis, cis-9,12-octadecanoyl, cis,cis,cis-9,12,15-octadecatrienoyl, arachinoyl, arachidonoyl or behenoyl.

7. A process according to claim 1, wherein the enzyme is immobilized.

8. A process according to claim 1, wherein the solvent is hexane or acetonitrile.

9. A process according to claim 1, wherein the reaction is carried out at a pressure below about 0.05 bar.

10. A process according to claim 1, wherein the glycoside moiety X—OCH$_3$ is present in α- or β-anomeric form or a mixture thereof.

11. A process according to claim 10, wherein the β-anomer is at least 10% of the mixture.

* * * * *